US012635681B1

(12) United States Patent
Gao et al.

(10) Patent No.: US 12,635,681 B1
(45) Date of Patent: May 26, 2026

(54) PEST DETECTION AND MONITORING PROBE IN A GRAIN STORAGE BIN

(71) Applicant: Ding Gao, London (CA)

(72) Inventors: Ding Gao, London (CA); Huan Wang, Haikou City (CN); Yao Yao, Zhengzhou City (CN)

( * ) Notice: Subject to any disclaimer, the term of this patent is extended or adjusted under 35 U.S.C. 154(b) by 0 days.

(21) Appl. No.: 19/083,148

(22) Filed: Mar. 18, 2025

(51) Int. Cl.
 *A01M 17/00* (2006.01)
 *A01M 13/00* (2006.01)
 *G01N 33/00* (2006.01)

(52) U.S. Cl.
 CPC ........ *A01M 17/008* (2013.01); *A01M 13/003* (2013.01); *G01N 33/0027* (2013.01)

(58) Field of Classification Search
 USPC ....................................................... 340/573.2
 See application file for complete search history.

(56) References Cited

U.S. PATENT DOCUMENTS

| | | | |
|---|---|---|---|
| 5,646,404 A | 7/1997 | Litzkow et al. | |
| 8,054,458 B2 * | 11/2011 | Baker ...................... | G01V 8/20 |
| | | | 250/341.7 |
| 8,806,772 B1 | 8/2014 | Schaefer, Jr. et al. | |
| 9,347,904 B1 * | 5/2016 | Schaefer, Jr. .......... | F26B 9/063 |
| 10,178,858 B2 * | 1/2019 | Azzarello ............ | A01M 1/2011 |
| 12,262,704 B2 * | 4/2025 | Qi ......................... | G01N 21/84 |

| | | | |
|---|---|---|---|
| 2011/0174072 A1 | 7/2011 | Pacheco Da Cunha | |
| 2013/0092432 A1 | 4/2013 | Crompton et al. | |
| 2017/0346953 A1 | 11/2017 | Abassi | |
| 2021/0123896 A1 * | 4/2021 | Barrettino ............ | G01N 33/246 |
| 2023/0067298 A1 | 3/2023 | Koch et al. | |
| 2023/0129551 A1 * | 4/2023 | Khir ...................... | A01M 1/026 |
| | | | 43/132.1 |
| 2023/0309536 A1 * | 10/2023 | Bonduelle ............. | A01M 1/103 |
| | | | 43/62 |

FOREIGN PATENT DOCUMENTS

| | | | | |
|---|---|---|---|---|
| CN | 107990942 A | | 5/2018 | |
| CN | 116311806 A | * | 6/2023 | ............ A01M 1/026 |
| CN | 220794480 U | | 4/2024 | |
| CN | 222564806 U | * | 3/2025 | |

* cited by examiner

*Primary Examiner* — Eric Blount
(74) *Attorney, Agent, or Firm* — Brunet & Co. Ltd.; Robert Brunet; Hans Koenig

(57) ABSTRACT

A pest detection and monitoring probe for monitoring pests in a grain storage bin is composed of: a rod insertable into a grain bed in the grain storage bin; a plurality of sensors connected to and supported by the rod, the plurality of sensors including: a temperature sensor for measuring temperature in the grain bed; a fumigant gas sensor for measuring concentration of a fumigant gas in the grain bed; and, a video camera for determining presence of pests in the grain bed and for monitoring motion of the pests in the grain bed; and, a signal transmission assembly connected to and supported by the rod, the signal transmission assembly in electronic communication with the plurality of sensors. Video monitoring of pest motion coupled with concentration measurement of the fumigant gas permits determining whether the dose of fumigant gas is too high or too low to kill the pests.

15 Claims, 3 Drawing Sheets

PEST DETECTION AND MONITORING PROBE IN A GRAIN STORAGE BIN

FIELD

This application relates to detection and monitoring of pests, for example insects, in a grain storage bin.

BACKGROUND

Pests, for example insects, arachnids and rodents, in a grain storage bin can cause loss of grain through consumption or spoiling of the grain through the spread of toxins and/or disease. As such, there is a need to be able to monitor conditions in a grain bed stored in the grain storage bin to be able to take appropriate action when pests are detected. A common action in a grain storage bin is to exterminate pests through the application of a fumigant gas (e.g., phosphine or a phosphine/oxygen mixture) when pests are detected. However, the application of the correct concentration of the fumigant gas is not necessarily a simple matter because the required concentration may be temperature dependent and at least some pests are only stunned and stop moving instead of being killed when too much fumigant gas is applied. Thus, there is often a narrow window of fumigant gas concentration that is effective, and over-dosing can lead to ineffective pest control. Current grain storage bin sensors rely on still cameras to detect the presence of pests. Given the difficulties in detecting whether pests have been killed during the fumigation process and the difficulties in determining the difference between a dead pest and a stunned pest after the fumigation process is complete, the use of still cameras can easily mislead the pest exterminators into believing that a fumigation process was successful. Further, once a determination has been made that the fumigation process was not successful, the pest exterminators will need to have sufficient information about environmental conditions in the grain bed to be able to determine what corrective efforts are needed.

There remains a need for a device and method for determining whether a fumigation process was successful in a grain storage bin, and if not, for providing sufficient data to be able to make corrective changes to the fumigation process.

SUMMARY

A method of exterminating pests in a grain storage bin comprises: detecting presence of the pests in a grain bed of the storage bin using a video camera; fumigating the grain bed with a fumigant gas; measuring a first concentration of the fumigant gas and a temperature in the grain bed during the fumigating; monitoring the pests with the video camera during the fumigating to determine whether the pests continue to move during the fumigating thereby determining that the concentration of the fumigant gas in the grain bed was insufficient to exterminate the pests; monitoring the pests with the video camera after the fumigating to determine whether the pests begin to move again thereby determining that the concentration of the fumigant gas in the grain bed was too high to exterminate the pests; and, if the pests continue to move during the fumigating or begin to move again after the fumigating, using the first concentration of the fumigant gas and the temperature in the grain bed to determine a second concentration of the fumigant gas to be applied to the grain bed to exterminate the pests.

A pest detection and monitoring probe for monitoring pests in a grain storage bin comprises: a rod insertable into a grain bed in the grain storage bin; a plurality of sensors connected to and supported by the rod, the plurality of sensors comprising: a temperature sensor for measuring temperature in the grain bed; a fumigant gas sensor for measuring concentration of a fumigant gas in the grain bed; and, a video camera for determining presence of pests in the grain bed and for monitoring motion of the pests in the grain bed; and, a signal transmission assembly connected to and supported by the rod, the signal transmission assembly in electronic communication with the plurality of sensors.

A system for detecting and monitoring pests in a grain storage bin comprises: the probe as defined above; and, a controller electronically connected to the probe, the controller configured to receive data from the plurality of sensors, the controller configured to utilize the data to determine if the pests are moving in the grain bed.

The probe comprises a plurality of sensors that measure environmental conditions in the grain bed. The plurality of sensors comprises a temperature sensor, a fumigant gas sensor and a video camera. Various fumigant gases for use on insects are known including carbon dioxide, oxygen, phosphine, hydrogen fluoride and mixtures thereof. In some embodiments, the fumigant gas sensor comprises one or more of a carbon dioxide sensor, an oxygen sensor, a phosphine gas sensor and a hydrogen fluoride gas sensor. In a preferred embodiment, the fumigant gas sensor comprises a phosphine gas sensor or both a phosphine and an oxygen sensor. In a preferred embodiment, the fumigant gas comprises phosphine or a mixture of phosphine and oxygen. In some embodiments, the plurality of sensors further comprises one or more other sensors, for example a relative humidity sensor, a liquid moisture sensor, a non-fumigant gas sensor and a still camera. Current sensors often combine temperature and moisture detection in a single unit. In some embodiments, the plurality of sensors comprises a material resistant to corrosive effects of the fumigant gas.

The probe comprises a rod that is insertable into a grain bed in a grain storage bin so that the plurality of sensors are able to sense conditions within the grain bed. In some embodiments, an end of the rod is configured to assist with insertion of the rod into the grain bed, for example, by providing the end with a shape that more easily penetrates the grain bed (e.g., a taper) or by providing the end with a boring device (e.g., an auger). The rod may have any cross-sectional shape, for example circular, elliptical, triangular, square, rectangular or the like. In some embodiments, the rod is solid, while in other embodiments, at least a portion of the rod is hollow. In some embodiments, a side of the rod is provided with one or more apertures through which one or more transmission cables extend connecting the signal transmission assembly to the plurality of sensors.

In some embodiments, the rod comprises a plurality of rod sections removably connected axially end-to-end. In some embodiments, the rod sections are removably connectable by connectors, for example, threaded connections (e.g., nuts and bolts, screws, or mated threaded portions of the rod walls), clamps, friction fit connections, tape, pins through aligned apertures in the rod sections when smaller diameter ends of the rod sections are fitted into larger diameter ends of other rod sections, etc. In a particular embodiment, the connector comprises a threaded male member at an end of a rod section and a matingly threaded female member at an end of another rod section. In some embodiments, each removable rod section supports a different sensor. The plurality of removable rod sections permits reconfiguration of the rod to contain different sensors and/or to have the sensors arranged in a different order. The heights of different sensors in the grain bed can be readily adjusted by changing the order of the rod sections. The plurality of removable rod sections may be packaged as a kit permitting customization of the rod in accordance with a user's needs. In some embodiments, the plurality of rod sections includes different removable bottom end sections with different configurations for assisting with insertion of the rod into the grain bed. In some embodiments, the plurality of rod sections includes different removable top end sections with different signal transmission assemblies to be able to customize the rod for different signal transmission modes. In some embodiments, the rod sections are provided with transmission cables having ends that are removably connectable to the transmission cables on neighboring rod sections. The rod can be adapted to a variety of grain storage bins, for example shallow round silos, bungalow silos and various simple silos, according to the different heights of the silos, and the appropriate number of rod sections are chosen to form a longer rod.

In some embodiments, the rod is a telescoping rod comprising a plurality of telescoping sections nested within each other.

In some embodiments, the probe comprises a sheath that can be fitted around the rod to protect the plurality of sensors from damage. In some embodiments, the sheath has ventilation apertures to permit better contact between the plurality of sensors and the conditions in the grain bed. In some embodiments, the sheath is provided with one or more fixing members, the one or more fixing members for securing the sheath to the rod. In some embodiments, the one or more fixing members comprises pins, (e.g., screws, bolts), clips or the like.

In some embodiments, the probe comprises a pest trap connected to the rod. In some embodiments, the pest trap comprises a hollow trapping tube and a collecting tube located below the hollow trapping tube, where the hollow trapping tube is in communication with the collecting tube so that pests can move from the trapping tube into the collecting tube. In some embodiments, the trapping tube is provided with a plug at an upper end thereof. In some embodiments, the trapping tube has a wall provided with trapping holes through which a pest can enter the trapping tube to fall into the collecting tube. In some embodiments, the video camera is positioned in relation to the pest trap to monitor the motion of the pests in the pest trap. In some embodiments, the probe comprises one or more lights configured to attract pests into the pest trap and/or to illuminate the pest trap to permit the video camera to monitor the motion of the pests in the pest trap. In some embodiments, at least one of the one or more lights is provided inside said the trapping tube. In some embodiments, the collecting tube is hollow at an upper portion of the collecting tube, and the bottom portion of the collecting tube is provided with a groove forming a pest collecting space. In some embodiments, the hollow portion of the collecting tube is connected to a lower end of the hollow trapping tube.

In some embodiments, the probe comprises one or more transmission cables connecting the signal transmission assembly to the plurality of sensors so that the signal transmission assembly is in electronic communication with the plurality of sensors, thereby permitting data from the plurality of sensors to be transmitted to the signal transmission assembly through the one or more transmission cables. In some embodiments, the one or more transmission cables are provided in sections that are removably connectable to others of the one or more transmission cables thereby providing the ability to extend or shorten a given transmission cable depending on distance between the signal transmission assembly and a given sensor. Providing sectional transmission cables facilitates rearranging the order of sensors on the rod when the rod comprises a plurality of rod sections removably connected axially end-to-end. In some embodiments, the rod is hollow so that the one or more transmission cables can extend inside the rod between the plurality of sensors and the signal transmission assembly.

In some embodiments, the signal transmission assembly comprises a wireless data transmission module comprising a radio frequency (RF) transmitter/receiver for wirelessly transmitting data collected by the plurality of sensors and for wirelessly receiving data from the controller. In some embodiments, the signal transmission assembly comprises wires through which data is transmitted between the signal transmission assembly and the controller. Whether the signal transmission assembly is wireless or wired, the signal transmission assembly transmits data to the controller and receives data from the controller, which is described below in connection with the system for detecting and monitoring pests in a grain storage bin. In some embodiments, the signal transmission assembly is connected to the rod by a connector, for example a threaded connection (e.g., nuts and bolts, screws, or mated threaded portions of the walls of the rod and the signal transmission assembly), tape, an adhesive, a clamp, a friction fitting, a flange or the like. The signal transmission assembly is preferably connected to the topmost (apical) portion of the rod and is preferably kept out of the grain bed when the probe is in use.

In some embodiments, the probe comprises an electrical power source connected to the rod and electrically connected to one or more of the plurality of sensors. In some embodiments, the electrical power source comprises a battery, a capacitor, a solar panel a wind turbine, or the like, or any combination thereof. Preferably, the electrical power source comprises a battery, for example a battery that is sufficient to power the video camera and other sensors for at least 24 hours. In some embodiments, the probe comprises an electrical power cord electrically connected to one or more of the plurality of sensors and electrically connectable to a power source remote from the probe, for example the mains of the grain storage bin or some other structure. In some embodiments, the electrical power cord is connected to the rod.

In some embodiments, the signal transmission assembly, the electrical power source and the controller are components of a data module connected to the rod.

The method of exterminating pests in a grain storage bin can be utilized with or without the probe or system described above. However, the probe and system are specifically designed to be able to perform the method in a routine and consistent manner that facilitates a fumigating operation in a grain storage bin. The method can be used to exterminate any pests (e.g., insects, arachnids, rodents and the like) in the grain bed in a grain storage bin. In some embodiments, the method is utilized to exterminate insects.

When using the probe or system, the presence of the pests in the grain bed of the storage bin is detected by the video camera. Video data collected by the video camera is transmitted to the controller and the data is assessed by the controller, or displayed for and assessed by an operator, to determine whether a fumigating operation is required. If a fumigating operation is required, the video data is utilized to determine information about the pests (e.g., species, lifestage, etc.) and together with grain bed temperature data, the information is used to determine which and how much (i.e., dosage of) fumigant gas is needed to exterminate the pests in the grain bed. In some embodiments, data related to the airtightness of the grain storage bin is also used when determining how much fumigant gas is needed. Poor air-tightness may necessitate a higher concentration of fumigant gas and a longer treatment period to ensure complete pest extermination. The grain bed is then fumigated with the fumigant gas. During fumigation, the concentration of the fumigant gas and the temperature in the grain bed are measured.

The pests are monitored with the video camera during the fumigating to determine whether the pests continue to move. If the pests continue to move during the fumigating, the concentration of the fumigant gas in the grain bed was insufficient to exterminate the pests. Based on the measured concentration of the fumigant gas and the temperature in the grain bed, the necessary dosage of fumigant gas is recalcu-lated and then the fumigating operation is repeated at the recalculated dosage of fumigant gas.

Once the fumigating operation is completed and the pests have stopped moving, the video camera continues to moni-tor the pests to determine whether the pests begin to move again. If the pests start to move again, the concentration of the fumigant gas in the grain bed was too high to exterminate the pests but only stunned the pests. Based on the measured concentration of the fumigant gas and the temperature in the grain bed, the necessary dosage of fumigant gas is recalcu-lated and then the fumigating operation is repeated at the recalculated dosage of fumigant gas.

The fumigating operation is conducted for a period of time up to a month, for example 5-28 days. Once the fumigating operation is fully completed and the pests have stopped moving even after monitoring the pests for contin-ued movement for several days after the fumigating opera-tion, the pests are considered exterminated.

There is an optimum dosage of fumigant gas that mini-mizes costs, prevents stunning the pests due to too high of a concentration and is effective at killing the pests at the temperature in the grain bed environment. For insects, 300 ppm of phosphine gas for 15 days is typical. However, the required fumigation time and gas concentration vary depending on the type of insects, the size of the grain storage bin, and the environmental conditions of the storage loca-tion. There is currently no universal standard. The method permits monitoring the effectiveness of the fumigating operation to ensure that the optimum dosage of fumigant gas is employed.

The system utilizing the probe described herein permits automating much or all of the fumigation assessment and operation to ensure the greatest efficiency of the method. The system comprises both hardware and software compo-nents. In some embodiments, hardware components com-prise the probe and the controller electronically. In some embodiments, software components comprise control soft-ware for performing the method, which may be embodied in the controller operatively linked to the plurality of sensors of the probe. The controller may also be operatively linked to other hardware components of an overall grain storage facility. In some embodiments, the controller is programmed to utilize the data to assess whether the fumigating is necessary and to execute the method utilizing fumigation equipment operatively connected to the controller. Elec-tronic communication may be provided through wires or wirelessly. The controller may comprise, for example, a computer, an output device and an input device, the com-puter comprising a microprocessor for controlling operations and a non-transient electronic storage medium for storing information about the grain bed and/or for storing computer executable code for carrying out instructions for implementing the method. The computer may further com-prise a transient memory (e.g. random access memory (RAM)) accessible to the microprocessor while executing the code. A plurality of computer-based apparatuses may be connected to one another over a computer network system and geographically distributed. One or more of the com-puter-based apparatuses in the computer network system may comprise a microprocessor for controlling operations and a non-transient electronic storage medium for storing information about the grain bed and/or for storing computer executable code for carrying out instructions for implement-ing the method, and the computer-based apparatuses in the network may interact so that the method may be carried out automatically from remote locations. The output device may be a monitor, a printer, a device that interfaces with a remote output device or the like. The input device may be a keyboard, a mouse, a microphone, a device that interfaces with a remote input device or the like. With a computer, data (e.g., temperature, fumigant gas concentration, video feed from the video camera, or data from any other sensor of the plurality of sensors) may be a graphically displayed in the output device. Computer readable code for executing com-puter executable instructions for carrying out the method may be stored on a computer readable non-transient storage medium.

In some embodiments, the fumigating operation is con-ducted using cyclone fumigation. Cyclone fumigation uti-lizes circular fumigation equipment to force fumigation gas circulation in the grain bed to promote rapid distribution of the fumigation gas in the grain bed. When the fumigant gas comprises phosphine, phosphine cyclone fumigation can be conducted in several ways, for example grain surface appli-cation, submembrane circulation and out-of-bin phosphine generation. Grain surface applications involve placing alu-minum phosphide on a surface of the grain bed, and then, with the help of a circular flow fan, phosphine gas generated from the aluminum phosphide is circulated through the grain bed. Submembrane circulation involves covering and seal-ing the surface layer of the grain bed in a grain storage bin with a film, and circulation is carried out by means of a circulation device, such as a return pipe placed under the film. Out-of-bin phosphine generation involves generating phosphine gas with a phosphine generator, which is propor-tionally mixed with carbon dioxide gas and then connected to the outside of the grain storage bin to circulate the gases in a circular flow pipe or vent.

In the method of exterminating pests in a grain storage bin, temperature data, pest data and fumigant gas concen-tration data are the most important data to collect. In some embodiments of the method, monitoring is automatically carried out by portable integrated grain testing equipment equipped with the system for detecting and monitoring pests in the grain storage bin before, during and after fumigation.

In some embodiments, before fumigation begins, the system calculates, according to previously collected data, the time of death of the pests, the fumigation time and the required fumigant dose (e.g., aluminum phosphide dose in cyclone fumigation grain surface application techniques) when the lethality of common pests (e.g., adult and larval forms of insects) in the grain storage bin is 100% at different grain bed temperatures and fumigant gas concentrations.

In some embodiments, during fumigation, the fumigation time is re-calculated based on information of the grain storage bin to be fumigated (e.g., volume, shape, airtightness), the monitored data of the target pests, the monitored grain bed temperature in the infested area, and a pre-set low-dose fumigant gas concentration, accounting for the time of mortality of the pests. In some embodiments, the initial fumigation dose and concentration calculations are based on the pre-set low-dose concentration, an initial dose of 56% aluminum phosphide tablets (when cyclone fumigation grain surface application is used), and other results based on the grain storage bin, target pests, and planned fumigation time. In some embodiments, the system automatically collects data and generates daily fumigation records and charts of grain temperature, fumigant gas concentration and pest lethality. If the fumigant gas concentration reaches the pre-set low-dose concentration, the system activates a pre-alarm and sends an alert notification to replenish the fumigant gas dosage, which is automatically performed by the system.

After fumigation, the system automatically generates a fumigation effect evaluation report based on relevant data, including pre-fumigation related data, which is used to refine predictions of various parameters including:

the lethality of the pests under conditions of grain bed temperature, fumigant gas concentration and fumigation time;

the fumigation time required for the pests at different lethality rates under different conditions of grain bed temperature and fumigant gas concentration; and, the concentration of fumigant gas (and dose of aluminum phosphide when cyclone fumigation grain surface application is used) required for the pests at different lethality rates under different conditions of grain bed temperature and fumigation time.

The method thereby permits recursive re-calculation of required fumigant gas doses and fumigation time for lethality of the pests under different conditions in the grain storage bin to ensure complete extermination of the pests in the grain storage bin.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which.

DETAILED DESCRIPTION

Figure 1:
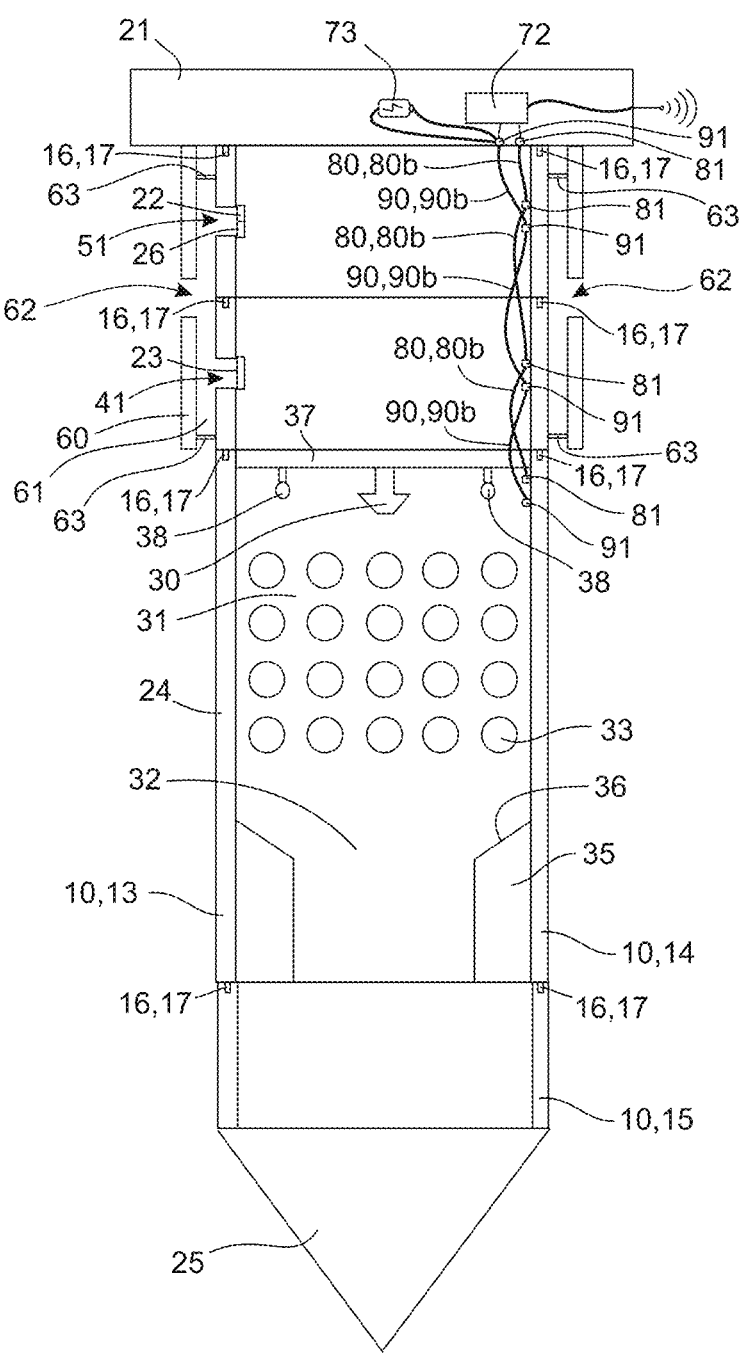
FIG. 1 depicts a schematic diagram of a pest detection and monitoring system comprising a pest detection and monitoring probe and a controller specifically for detecting and monitoring insects in a grain storage bin.
Figure 1:
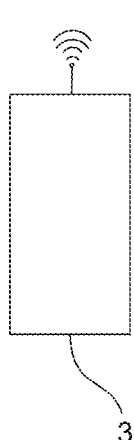

FIG. 1 depicts a pest detection and monitoring system 1 comprising a pest detection and monitoring probe 2 specifically for detecting and monitoring insects in a grain storage bin and a remotely located programmable controller 3.

Figure 2:
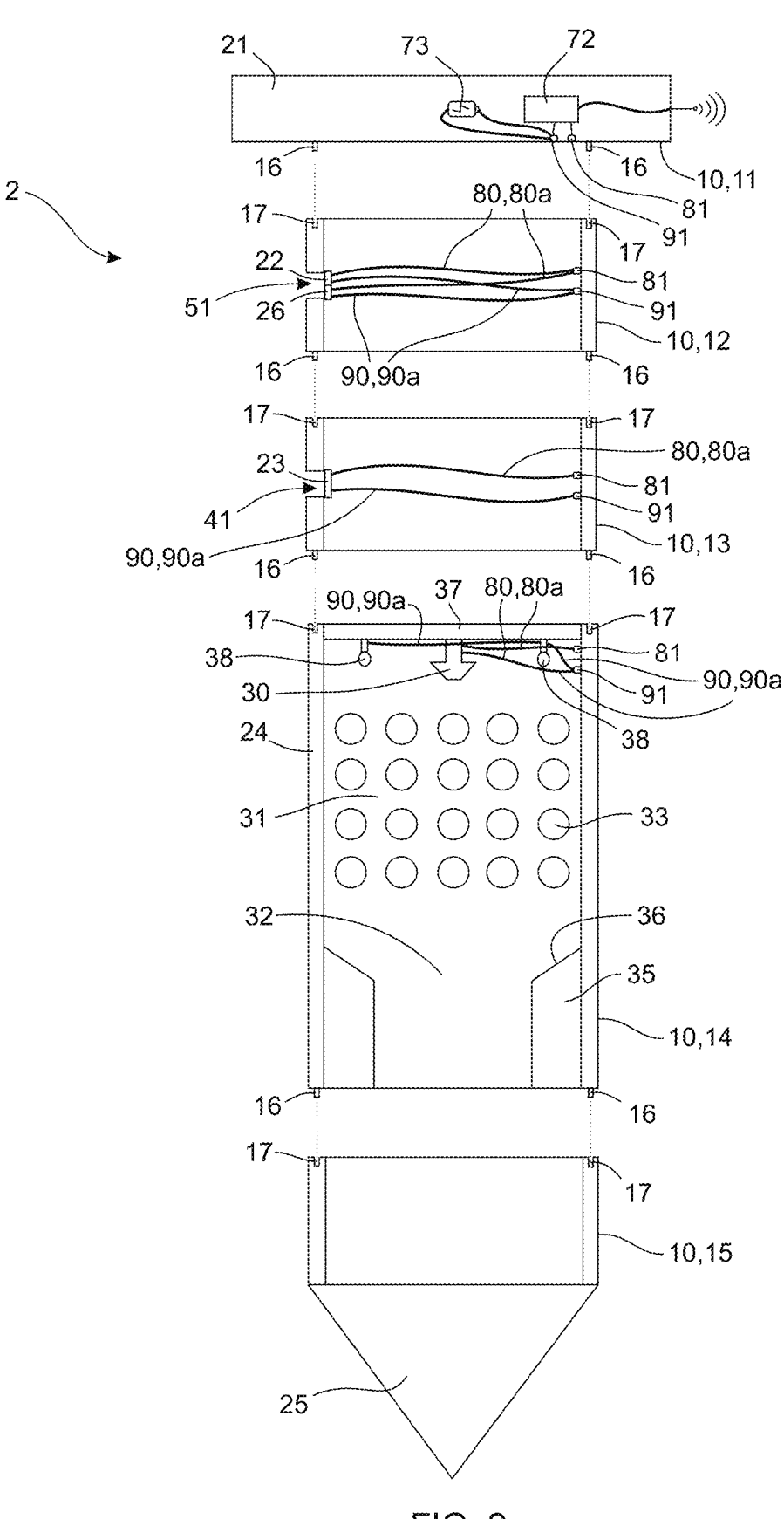
FIG. 2 depicts an exploded view of the probe shown in FIG. 1 without a sheath and showing rod sections separated from each other.
Figure 3A:
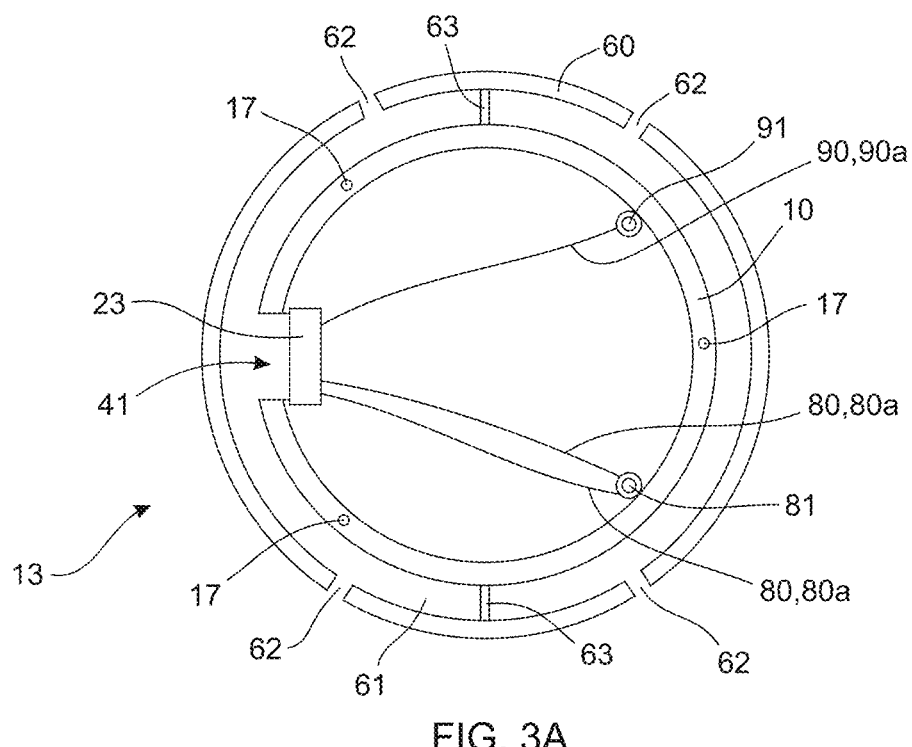
FIG. 3A depicts a top end view of a rod section of the probe shown in FIG. 2.
Figure 3B:
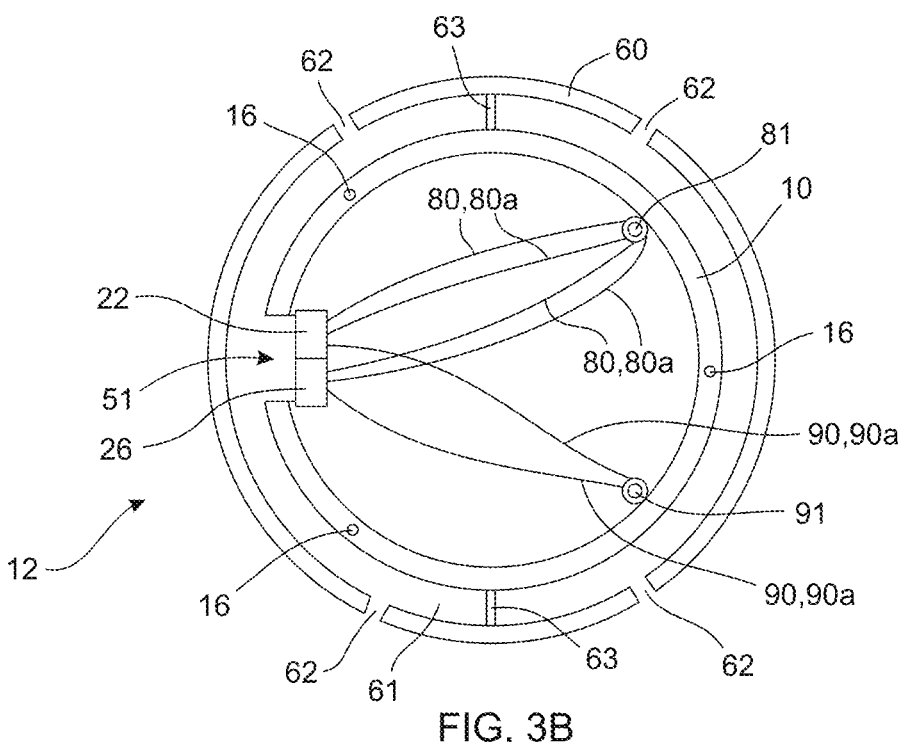
FIG. 3B depicts a bottom end view of a rod section that connects to the top end of the rod section shown in FIG. 3A.

The probe 2 comprises a cylindrical rod 10 comprising five removably connected rod sections 11, 12, 13, 14 and 15 that are connected axially end-to-end to form the rod 10. FIG. 2 depicts an exploded view of the probe 2 shown in FIG. 1 showing the rod sections 11, 12, 13, 14 and 15 separated from each other. The rod section 11 is apical and comprises a signal transmission assembly 21. The rod section 12 is axially connected to the rod section 11, the rod section 12 comprising a temperature sensor 22 and a humidity sensor 26. The rod section 13 is connected axially to the rod section 12, the rod section 13 comprising a phosphine gas sensor 23. The rod section 14 is connected axially to the rod section 13, the rod section 14 comprising an insect trap 24 comprising a video camera 30. The rod section 15 is connected axially to the rod section 14, the rod section 15 comprising a tapered tip 25 to facilitate inserting the rod 10 into a grain bed in the grain storage bin. The rod sections 11, 12, 13, 14 and 15 are connected together by friction fits between male fittings 16 and female fittings 17 on end faces of the rod sections 11, 12, 13, 14 and 15. FIG. 3A depicts a top end view of the rod section 13 showing three female fittings 17 (e.g., holes) distributed around a top face of the rod section 13. FIG. 3B depicts a bottom end view of the rod section 12 that releasably connects to the top end of the rod section 13, a bottom face of the rod section 12 comprising three corresponding male fittings 16 (e.g., pins) that mate with the three female fittings 17 to provide a friction fit that holds the two rod sections 12, 13 together. The other rod sections 11, 14 and 15 are releasably held to neighboring rod sections in a similar manner.

The insect trap 24 comprises a hollow trapping tube 31 and a hollow collecting tube 32. The collecting tube 32 is in communication with and located below the trapping tube 31 when the probe 2 is in use so that insects trapped by the trapping tube 31 fall into the collecting tube 32. Both the trapping tube 31 and the collecting tube 32 are formed by hollow portions of the rod section 14. The trapping tube 31 comprises a plurality of apertures 33 (only one labeled) in and around the cylindrical wall of the trapping tube 31, the apertures 33 having sufficient diameter to permit insects to enter through the apertures 33 into the trapping tube 31 where they fall down into the collecting tube 32. The collecting tube 32 comprises an interior annular boss 35 having a beveled upper rim 36, annular boss 35 providing a groove forming a pest collecting space. A top of the insect trap 24 comprises a plug 37 to prevent insects from potentially migrating upward into the rod section 13. Connected to an underside of the plug 37 is the video camera 30 that has a lens sufficient to provide a view of the interiors of both the trapping tube 31 and the collecting tube 32. A pair of lights 38 are also connected to the underside of the plug 37 to both attract the insects into the trapping tube 31 and to illuminate the insects in both the trapping tube 31 and the collecting tube 32 so that the video camera 30 can capture better images of the insects.

The phosphine gas sensor 23 is located inside the rod section 13 and mounted to an interior wall of the rod section 13. The wall of the rod section 13 where the phosphine gas sensor 23 is mounted comprises a through-aperture 41 permitting the environment in the grain bed to contact the phosphine gas sensor 23 so that the phosphine gas sensor 23 can sense the concentration of phosphine gas in the grain bed.

The temperature sensor 22 and the humidity sensor 26 are located inside the rod section 12 and mounted to an interior wall of the rod section 12. The wall of the rod section 12 where the temperature sensor 22 and the humidity sensor 26 are mounted comprises a through-aperture 51 permitting the environment in the grain bed to contact the temperature sensor 22 and the humidity sensor 26 so that the temperature sensor 22 and the humidity sensor 26 can sense the temperature and relative humidity, respectively, in the grain bed.

A sheath 60 situated around the rod 10 to surround the rod sections 12 and 13 protects the phosphine gas sensor 23, the temperature sensor 22 and the humidity sensor 26 from damage. The sheath 60 is separated from the rod 10 by a gap 61 and apertures 62 in the sheath 60 permits the communication between the gap 61 and the environment in the grain bed while the through-apertures 41 and 51 in the rod sections 13 and 12, respectively permit communication between the gap 61 and the phosphine gas sensor 23, the temperature sensor 22 and the humidity sensor 26. An inner wall of the sheath 60 is fixed to an outer wall of the rod 10 by a plurality of fixing members 63, for example clips or screws.

The signal transmission assembly 21 comprises a housing 71 connected to a top end of the rod section 12. The housing 71 contains a radio frequency (RF) transmitter/receiver 72 for transmitting and receiving RF signals to and from the remotely located controller 3. Transmission cables 80 are used to electronically connect the signal transmission assembly 21 to the video camera 30 and the other sensors 23, 22, 26. The transmission cables 80 comprise short sections 80*a* (not shown in FIG. 1) that electronically join the sensors 30, 23, 22, 26 to data transmission ports 81 mounted in respective rod sections 14, 13, 12, 11. The transmission cables 80 also comprise short sections 80*b* (not shown in FIG. 2, FIG. 3A and FIG. 3B) that electronically join the data transmission ports 81 between neighboring rod sections. The transmission cables 80 run in and through the hollow rod sections 12 and 13 between the rod section 11 and the rod section 14 to connect the signal transmission assembly 21 to all the sensors 30, 23, 22, 26. The transmission cables 80 are joined to the transmission ports 81 by pin and socket connections at the transmission ports 81 in each rod section. The transmission ports 81 and the short sections 80*a*, 80*b* of the transmission cables 80 contribute to the reconfigurability of the rod 10.

The housing 71 also contains a battery 73 for powering the video camera 30, the other sensors 23, 22, 26 and the lights 38. Power cords 90 are used to electrically connect the battery 73 to the video camera 30, the other sensors 23, 22, 26 and the lights 38. The power cords 90 comprise short sections 90*a* that electrically join the sensors and lights 30, 23, 22, 26, 38 to power ports 91 mounted in respective rod sections 14, 13, 12, 11. The power cords 90 also comprise short sections 90*b* that electrically join the power ports 91 between neighboring rod sections. The power cords 90 run in and through the hollow rod sections 12 and 13 between the rod section 11 and the rod section 14 to connect the battery 73 to all the sensors and lights 30, 23, 22, 26, 38. Thus, the power cords 90 are joined to the power ports 91 by pin and socket connections at the power ports 91 in each rod section. The power ports 91 and the short sections 90*a*, 90*b* of the power cords 90 contribute to the reconfigurability of the rod 10.

In an embodiment of a method of exterminating insects in a grain storage bin, the system 1 is employed to detect the presence of the insects, measure first and second concentrations of phosphine fumigant gas, measure the temperature and humidity, and monitor the insects during and after applying the phosphine gas. The controller 3 of the system 1 is programmed to utilize the data to assess whether the fumigating is necessary and to execute the method utilizing fumigation equipment operatively connected to the controller 3.

In the method, the rod sections 11, 12, 13, 14 and 15 are fitted together, including connecting sequential transmission ports 81 with transmission cables 81*b* and connecting sequential power ports 91 with power cords 91*b*, in the order shown in FIG. 1 and FIG. 2. The rod 10 ins inserted into the sheath 60 and the sheath 60 is secured to the rod 10 by fixing elements 63 to form the probe 2. The probe 2 is inserted into the grain bed and the controller 3 electronically communicates wirelessly with the signal transmission assembly 21 through the transmitter/receiver 72 providing instructions to switch on the sensors 30, 23, 22 and 26, as well as the lights 38. The signal transmission assembly 21 then starts receiving data signals from the sensors 30, 23, 22 and 26 through the transmission cables 80 and transmits the data signals back to the controller 3 for signal processing and interpretation.

When the video camera 30 detects the presence of the insects in the insect trap 24, the video data collected by the video camera 30 is transmitted to the controller 3 and the data is assessed by the program in the controller 3 to determine whether a fumigating operation is required. If a fumigating operation is required, the video data is utilized to determine information about the insects (e.g., species, life-stage, etc.) and together with grain bed temperature data collected by the temperature sensor 22, the information is used by the program to calculate how much (i.e., dosage of) phosphine gas is needed to exterminate the insects in the grain bed. The controller 3, being operatively linked to fumigating equipment, then conducts the fumigating operation dosing the grain bed with phosphine gas at the calculated dose. During fumigation, the concentration of the phosphine gas and the temperature are monitored by the phosphine gas sensor 23 and the temperature sensor 22, respectively, and the data is transmitted to the controller 3 through the signal transmission assembly 21.

The insects are continuously monitored with the video camera 30 during the fumigating and the video data is transmitted to the controller 3, which determines whether the insects continue to move. If the insects continue to move during the fumigating, the concentration of the phosphine gas in the grain bed was insufficient to exterminate the insect. Based on the measured concentration of the phosphine gas and the temperature in the grain bed, the necessary dosage of phosphine gas is recalculated by the controller 3 and then the controller 3 repeats a fumigating operation at the recalculated dosage of phosphine gas.

Once the fumigating operation is completed and the controller 3 determines from the video data collected by the video camera 30 that the insects have stopped moving, the video camera 30 continues to monitor the insects in the insect trap 24 providing video data to the controller 3, which determines whether the insects eventually begin to move again. If the controller 3 determines from the video data that the insects start to move again, the concentration of the phosphine gas in the grain bed was too high to exterminate the insects but only stunned the insects. Based on the measured concentration of the phosphine gas and the temperature in the grain bed, as determined by the controller 3 from the data transmitted from the phosphine gas sensor 23 and the temperature sensor 22, the necessary dosage of phosphine gas is recalculated and then the fumigating operation is repeated by the controller 3 at the recalculated dosage of phosphine gas.

Once the fumigating operation is completed and the insects have stopped moving even after monitoring the insects for continued movement for several hours after the fumigating operation, the insects are considered exterminated.

The novel features will become apparent to those of skill in the art upon examination of the description. It should be understood, however, that the scope of the claims should not be limited by the embodiments but should be given the broadest interpretation consistent with the wording of the claims and the specification as a whole.

The invention claimed is:

1. A system for detecting and monitoring pests in a grain storage bin, the system comprising:
a probe comprising:
a rod insertable into a grain bed in the grain storage bin;
a plurality of sensors connected to and supported by the rod, the plurality of sensors comprising:
a temperature sensor for measuring temperature in the grain bed;
a fumigant gas sensor for measuring concentration of a fumigant gas in the grain bed; and,
a video camera for detecting presence of pests in the grain bed and for monitoring motion of the pests in the grain bed; and,
a signal transmission assembly connected to and supported by the rod, the signal transmission assembly in electronic communication with the plurality of sensors; and,
a controller electronically connected to the probe, the controller configured to receive data from the plurality of sensors, the controller configured to utilize the temperature in the grain bed, the concentration of the fumigant gas in the grain bed and the motion of the pests in the grain bed to determine if the pests are moving in the grain bed, to determine whether the concentration of the fumigant gas in the grain bed was insufficient to exterminate the pests and to determine a second concentration of the fumigant gas to be applied to the grain bed to exterminate the pests if the pests continue to move in the grain bed.

2. The system of claim 1, wherein the pests comprise insects.

3. The system of claim 1, wherein the fumigant gas comprises phosphine gas.

4. The system of claim 1, wherein the fumigant gas sensor comprises a phosphine gas sensor.

5. The system of claim 1, wherein the plurality of sensors comprises a material resistant to corrosive effects of the fumigant gas.

6. The system of claim 1, further comprising a pest trap connected to the rod, the video camera positioned in relation to the pest trap to monitor the motion of the pests in the pest trap.

7. The system of claim 6, further comprising one or more lights configured to attract pests into the pest trap and/or to illuminate the pest trap to permit the video camera to monitor the motion of the pests in the pest trap.

8. The system of claim 1, further comprising an electrical power source connected to the rod and electrically connected to one or more of the plurality of sensors.

9. The system of claim 8, wherein the electrical power source comprises a battery.

10. The system of claim 1, further comprising an electrical power cord, electrically connected to one or more of the plurality of sensors and electrically connectable to a power source remote from the probe.

11. The system of claim 1, wherein the rod comprises a plurality of rod sections removably connected axially end-to-end.

12. The system of claim 1, wherein the plurality of sensors further comprises one or more of a relative humidity sensor, a liquid moisture sensor and a non-fumigant gas sensor.

13. The system of claim 1, further comprising one or more transmission cables connecting the signal transmission assembly to the plurality of sensors so that the signal transmission assembly is in electronic communication with the plurality of sensors.

14. The system of claim 1, wherein the signal transmission assembly comprises a wireless data transmission module comprising a radio frequency (RF) transmitter/receiver for wirelessly transmitting data collected by the plurality of sensors.

15. The system of claim 1, wherein an end of the rod comprises a taper or an auger to assist with insertion of the rod into the grain bed.

* * * * *